United States Patent

Hall

[11] Patent Number: 6,072,853
[45] Date of Patent: Jun. 6, 2000

[54] MATERIAL ANALYSIS

[75] Inventor: Christopher Hall, Stapleford, United Kingdom

[73] Assignee: Schlumberger Technology Corporation, Sugar Land, Tex.

[21] Appl. No.: 09/043,493

[22] PCT Filed: Sep. 26, 1998

[86] PCT No.: PCT/GB96/02408

§ 371 Date: Jun. 8, 1998

§ 102(e) Date: Jun. 8, 1998

[87] PCT Pub. No.: WO97/12234

PCT Pub. Date: Apr. 3, 1997

[30] Foreign Application Priority Data

Sep. 27, 1995 [GB] United Kingdom .................. 9519687

[51] Int. Cl.[7] ............................................. G01N 23/30
[52] U.S. Cl. .............................................. 378/73; 378/71
[58] Field of Search .......................................... 378/70–81

[56] References Cited

U.S. PATENT DOCUMENTS 3,903,415  9/1975  Holzapfel .
5,136,624  8/1992  Schneider et al. ................... 378/73

FOREIGN PATENT DOCUMENTS 0 354 045  2/1990  European Pat. Off. .

OTHER PUBLICATIONS

H.F. Poulsen et al., *Amorphous Silica Studied by High Energy X–ray Diffraction*, Journal of Non–Crystalline Solids, 188 (1995) pp. 63–74.

Kazuhiko Tsuji et al., *Measurements of X–ray Diffraction for Liquid Metals Under High Pressure*, Review of Scientific Instruments, vol. 60, No. 7, (Jul. 1989), New York, pp. 2425–2428.

K. G. Huang, et al. *Argonne National Laboratory X6B Beamline at NSLS: A Versatile Facility*, Review of Scientific Instruments, vol. 66, No. (Feb. 1995), New York, pp 1688–1690.

T. I. Morrison, et al., *Potential Opportunities for Materials Research at the Advanced Photon Source*, Nuclear Instruments and Methods in Physics Research, vol. 97, (May 1995), pp. 515–517.

*Primary Examiner*—Craig E. Church
*Attorney, Agent, or Firm*—William B. Batzer

[57] ABSTRACT

A method and apparatus for analyzing drill core rock samples is described, utilizing a collimated beam of polychromatic X-ray photons of a brightness of at least $10^{15}$ photons/sec/mrad$^2$/0.1% bandwidth and energies of at least 20 keV. A suitable source of such X-rays is a synchrotron.

15 Claims, 4 Drawing Sheets

MATERIAL ANALYSIS

This invention relates to material analysis, and concerns in particular methods of analysing crystalline mineral materials using X-ray diffraction pattern techniques.

It is common to analyse crystalline materials using a technique that involves making an X-ray diffraction pattern from the material and comparing this with similar, reference patterns derived from known materials. The diffraction pattern for any crystalline substance is characteristic of the atomic elements making up the substances, the ways these are regularly arranged within the crystal (the crystal lattice), and the overall structure of the crystal (the various lattice planes therewithin, and especially the distance of separation between these). The lattice forms a diffraction grating the spacing of which is of a size that will result in the diffraction of very short wavelength, very high frequency electromagnetic radiation passing through the crystal; indeed, the grating size is so small that a useful diffraction pattern can only be obtained using X-rays, photons which have wavelengths of the order of 1 nanometre ($10^{-9}$ metre) and below.

The use of this X-ray diffraction pattern technique is of particular value in the analysis of multi-phasic materials—that is, materials which are compositions of several different sorts of substances—where it is required to identify the individual phases and determine how much of each is present. Typical solid multi-phasic materials that can be handled by the technique are both natural bodies such as rocks and also artificial substances such as cements, ceramics, and metals and their alloys.

At present it is routine to make X-ray diffraction patterns using versions of this method that differ essentially only in employing one or other of two basic physical forms of material and looking either at transmitted (forward scattered) or reflected (backward scattered) X-rays. In the first version, which is perhaps conceptually the simplest, a spot on the face of a very thin slice of the material under study is illuminated by a narrow, parallel (collimated) beam of monochromatic (single wavelength) X-rays, and the diffracted X-rays transmitted (forward scattered) through the slice and coming out from the spot at different angles are picked up and measured (as regards their intensity) by a detector that scans slowly across the fan of X-rays emanating from the sample's reverse face. The manner in which the intensity of the transmitted X-rays varies as the scanner moves, and the angle changes, forms the desired diffraction pattern, and is, as noted above, characteristic of the material. In the second version of the method a sample of the material, commonly but not necessarily in the form of a compressed powder, is similarly illuminated, and the fan of reflected X-rays is similarly scanned (most rocks are effectively compressed or compacted powders; provided the illuminated spot includes a sufficiently large number of randomly-oriented individual crystallates, a powder material is, on the atomic scale involved, little different for this purpose from a simple slice, and is often much more convenient to prepare and deal with). The second version permits the surface identification of a thick sample (such as a rock drill core), but because of the very limited penetration ability of the X-rays presently used provides no information about the material within the sample.

Analysis by X-ray diffraction pattern has been very effectively utilised for many years. In the oil industry, for instance, it has been employed to determine the precise nature of the formations through which an oil well borehole is to pass (drill core samples are advantageously analysed using this technique). There are, nevertheless, serious problems with the present implementations of the procedure. Firstly, the method is a destructive one, for it necessarily involves the original material sample—a drill core, for instance—being structurally destroyed, by being either cut into slices or powdered. In itself, such destruction means that the sample in its real form is lost for ever—and, indeed, perhaps that it cannot additionally later be tested/measured in some other physical manner. Moreover, in the analysis of earth formation drill cores this slicing or powdering may be highly undesirable from a different, though related, reason; much information about the rock resides in the macro structure of the sample, and particularly in its heterogeneity, both laterally, across the core, and longitudinally (the internal striations, or layering, along the core), most of which is lost if the core is sliced or powdered unless many time-wasting repetitions of the analysis are made for very small samples.

Secondly, the technique in its present form is extremely time-consuming. The usual commercial sources of X-rays are relatively weak (with a low intensity, or brightness), monochromatic (single frequency), and of low penetrating capability. Their weakness and poor penetration means that for a transmission diffraction pattern the slice or powder layer must be very thin indeed or no X-rays will penetrate at all, while for a reflection diffraction pattern only the surface of the sample provides useful information. Moreover, even in these cases the "beam" of transmitted or reflected X-rays is so dim—the number of X-ray photons coming out is so small in a given time—that detecting it and getting a signal sufficiently strong to produce a well-defined diffraction pattern is both difficult and lengthy. And furthermore, the use of a monochromatic source necessarily requires the detector to scan extremely slowly across the fan of X-rays—perhaps as slowly as one minute of arc in a second of time (which is one degree per minute)—to gather all the available information about the diffracted X-rays. Utilising a weak, monochromatic source may require the sample to be illuminated for many hours just to produce one usable diffraction pattern; fully to characterise a core sample like this might require tens or even hundreds of such patterns to be made, with total times measured in days, even weeks. The invention proposes a modified form of the technique which not only can be applied non-destructively but also is extremely rapid, such that a single diffraction pattern can be obtained in mere minutes, even seconds, and a useful length of core fully characterised in a few hours, even minutes.

The present invention stems from the realisation that the disadvantages and inconveniences of the present methods are derived from the nature of the X-rays used—and of the source thereof. More specifically, the problems of the methods in use today are caused by the relative weakness of the X-ray beams used, by the relatively low frequency of these X-rays, and by their monochromatic nature—for example, around $10^9$ photons/sec at 7.5 keV using a conventional copper rotating anode source. Were the X-rays to be more brilliant—more intense—then there would be more diffracted X-ray photons, and gathering them would be easier and quicker. Were the X-rays to be of a higher, more penetrating frequency then not only would more of them be diffracted and transmitted (giving a stronger output to the detector) but they would be able to penetrate a thicker slice or layer, maybe even the entire width of a core (about 2.5 cm, or 1 inch), so that the core would not need to be destructively cut up into slices, or powdered, but could be illuminated whole and in one re-usable piece, from the side. Moreover, with an energetic, penetrating beam of X-rays it would be possible, using a collimator, to arrange that the detector "look" along a line of the output diffracted X-rays that intersected with the illuminating beam line at a very small spot—a roughly lozenge-shaped volume—actually within the sample itself, and so gather relatively high resolution data about the very innards of the sample. And were the X-rays to be polychromatic (composed of many different frequencies) it would not be necessary to scan the sample at all, for, with such a source, keeping the scanner in one place, looking at the sample at one angle only, and distinguishing the diffracted X-rays by their frequency (in practice, their energy) would provide the same sort of information as is gained using a monochromatic source and scanning across the sample to distinguish the X-rays by their angle.

Such X-ray sources exist; an example is a synchrotron, a device in which electrons are driven, by pulsing electric fields synchronised with the passage of the electrons therethrough, at very high speed in a generally circular path constrained by strong magnetic fields, and at intervals around their track are forced abruptly to change direction, which change causes them to emit the desired X-ray radiation. These X-rays are photons commonly in the energy range 30,000 to 130,000 electron Volts (30 to 130 keV), which corresponds to a wavelength range of 0.04 to 0.01 nm, and their intensity (or brightness or brilliance), measured as photon flux, can be of the order of $10^{12}$ photons/sec/mm$^2$ in a 0.1% bandwidth at 50 keV. The invention proposes, therefore, the use of a source of this general sort to provide X-ray diffraction patterns of crystalline materials, especially those found in earth formations (as sampled in the form of a drill core).

In one aspect, therefore, the invention provides a method of determining characteristics of a test crystalline material, in which method:

a sample of the material is illuminated with a collimated beam of polychromatic X-ray photons of a brightness of at least $10^{15}$ photons/sec/mrad$^2$/0.1% bandwidth and energies of at least 20 keV, to produce diffracted X-rays;

measurements are taken of the produced diffracted X-rays with an energy-dispersive detector receiving them via a collimator; and by comparing the found measurements with similar data defining known, reference materials, there are determined the required characteristics of the test material.

The invention provides a method of determining characteristics of a test crystalline material. The specific characteristics determinable will depend to some extent on the nature and form of the test material. Basically, however, and according to the same general principles utilised when interpreting X-ray diffraction patterns made employing conventional X-ray sources, the method allows there to be ascertained the composition and crystalline structure of the test material—that is to say, (by inference) the atoms from which the material is made, and the manner in which those atoms are combined into compounds, and (directly) the organisation of those compounds into the crystals that form the body of the sample. For example, when applied to a typical earth formation encountered when drilling for oil the method might show that the sample was made up of calcite with minor amounts of dolomite (and hence is classified as a dolomitic limestone), or it might show that it was made up of quartz, feldspars and several clays individually identified as chlorite, illite and kaolinite (and hence is classified as a sandstone). The method would show the relative amounts of the various constituent materials.

The invention's method is primarily for determining characteristics of a solid test crystalline material, as typified by the rocks in a drill core, the stone of a building or of a fossil, the concrete of a bridge (or the cement of a well casing), the metal plate forming the armour of a tank or ship, and—in a medical situation—a tooth or a bone. These are bulk solids—relatively large chunks of material—and most of them are polycrystalline and with some internal structure. However, the method can also be applied to test materials which are "soft solid" or even "liquid"—as, for example, a mixture of small crystalline particles of a real solid in a flowable solid material such as a polymer or dispersed clay, or a suspension of small particles of a real solid in a real liquid.

In the method of the invention a sample of the test material is illuminated with X-rays. The sample may take any form—indeed, it can be a thin slice or a powder, as is the case in the preparation of conventional X-ray diffraction patterns—but the major advantage of the present invention, stemming from the use of X-rays having high intensities and frequencies, is that these X-rays have very considerable penetrating power, and so can actually be employed with success on relatively large—that is, thick—samples. Specifically, when the sample is an earth formation of the type constituted by a drill core it may actually be the core itself. Such drill cores are commonly cylinders around 2.5 cm (1 in) in diameter, and the preferred X-rays can penetrate right through the core, from one side to the other, to produce a corresponding beam of diffracted X-rays that is still strong enough to result in the production (by the detector system) of useful information within a few seconds.

The test material sample is illuminated with a collimated beam of X-rays—that is to say, there is shone onto the sample a parallel beam of X-rays. To result in useful information the beam needs to be parallel (or very nearly parallel) so that the exact relationship between the direction of the illuminating beam and the direction of the diffracted beam—that is, the angle therebetween, is well defined (for the correct interpretation of the generated diffraction pattern it is essential to know this angle). The manner in which such a parallel beam is provided will depend upon the nature of the source (see below); if the source is a synchrotron then at the relevant station around the synchrotron the emitted X-rays will naturally be very nearly parallel, and can be made sufficiently so by passing the emitted beam through a sequence of fine slits until the output is effectively parallel.

When analysing a sample it is usually desirable to know accurately the nature of a small portion of the sample, and to make many such determinations of many different such small portions to gain an understanding of the sample as a whole, and the way it may vary from portion to portion, rather than to obtain general but less specific information about the whole sample in one go. The smaller the portions the higher the resolution of the system, and the more detail the method reveals. For such a high resolution system the beam needs to be reasonably narrow—the narrower the beam the smaller the illuminated portion, the higher the resolution of the system and the more accurately the results indicate the details of the sample. In the method of the invention beam widths of from 0.5 to 0.02 mm are desirable, with beams at the narrower end of the range—say, of around 0.05 mm—preferred where the highest resolution is required.

The method of the invention employs X-rays of an intensity corresponding to at least $10^{15}$ photons/sec/mrad$^2$/0.1% bandwidth. Together with the X-rays' frequency it is the intensity—the brightness of the beam—which determines the intensity of the outcoming diffracted beam—that is, the number of X-ray photons that come out in a given time. And of course it is this latter that governs the time taken for the detection system collecting and measuring the diffracted X-rays to produce useful information. Basically, then, the higher the intensity the more diffracted X-rays are collected and measured in a shorter time, and the more convenient the method becomes. Of course, the intensity of the diffracted X-rays also depends upon the thickness of the sample, so that a relatively lower intensity source may suffice for a relatively thin sample while a higher intensity source is needed for a thicker sample. For samples of about 1 cm (0.5 in) thickness illuminating X-rays of intensity $10^{17}$ photons/sec/mrad$^2$/0.1% bandwidth will usually produce good results in an acceptably short time—say, a few seconds. In most practical cases the X-ray sources employed produce a range of intensities.

The invention's method employs X-ray photons having energies of at least 20 keV. X-rays are usually regarded as the radiation that lies in the electromagnetic spectrum in the region from 10 nm down to 0.01 nm. In the invention, though, the preferred X-rays are those towards the lower end of this range—that is, photons having wavelengths below about 1 nm—and it is these that have the required energies. It is the use of photons with such high energies (and thus low wavelengths and high frequencies) which determines the penetrating power of the X-rays, and therefore which, together with the intrinsic brightness/intensity of the illuminating beam, determines the intensity of the outcoming diffracted beam. Basically, then, the higher the photon energies (the higher the frequency, and the lower the wavelength) the further the X-rays can penetrate and the more diffracted X-rays are collected and measured in a shorter time—and so the more convenient the method becomes. Again, a relatively lower energy/frequency source may suffice for a relatively thin sample while a higher energy/frequency source is needed for a thicker sample. There is, however, another factor to take into account. As noted above, using monochromatic (single frequency) X-rays it is necessary, to obtain the desired information—the diffraction pattern information—to scan the detector system across the output diffracted X-rays to pick them up over a range of angles. For a very high resolution scan monochromatic X-rays, being easier to produce in a very narrow beam, are perhaps the best. However, if the X-rays are polychromatic (composed of many different frequencies) it will not be necessary to spend substantial time scanning the sample, but instead simply to keep the scanner in one place, looking at the sample at one angle only, and then to distinguish the information-providing transmitted X-rays by their frequency rather than their angle. For this reason the illuminating X-rays utilised in the method of the invention are polychromatic. In most practical cases the X-ray sources employed produce a suitable range of energies/frequencies.

The beam of X-rays used in the method of the invention is constituted by photons of an intensity of at least $10^{15}$ photons/sec/mrad$^2$/0.1% bandwidth and an energy of at least 20 keV. At present the sources of X-rays having these characteristics are synchrotrons (though much research is currently being undertaken to provide other such sources—for example, plasmas and lasers. A synchrotron typically outputs X-ray with an energy distribution of from around 20 to 150 keV—and a fairly uniform, flat distribution in energy levels ranging from around 30 to 130 keV. Though the available synchrotrons throughout the world are very large and very expensive installations, and so are fairly few in number, nevertheless they are a suitable, commercial source—time can be purchased on the UK Synchrotron Radiation Sources at the Daresbury Laboratory, as it can on the rather larger and more powerful European Synchrotron Radiation Facility at Grenoble, each of which incorporates many "stations" at which a sample to be analysed can be illuminated by whatever instance of X-ray beam is desired.

The method of the invention involves taking measurements of the produced diffracted X-rays, and then comparing what is found against the values for known, reference materials. These measurements are primarily of the intensity of the diffracted X-rays and of either their frequency/energy or their angle. From these parameters can be built up a diffraction pattern—which may if appropriate be displayed in a human-readable form, such as a graph of intensity against frequency or angle—which can later be compared with the patterns obtained from (or computed for) known, reference materials so as to enable an identification of the (unknown) test material. In the method of the invention the apparatus used for these measurements is not a conventional detector but is instead an energy-dispersive detector—that is, it is a detector that not only detects (and counts) the received X-ray photons but also "measures" the energy of each and separates them into groups depending on their energy. In this way the components of a diffracted polychromatic beam of X-rays can be sorted into frequency/energy bands, allowing the required "full-spectrum" diffraction pattern to be obtained without the need to scan the detector across the fan of output X-rays.

Energy-dispersive detectors take a number of forms, but in a typical case the key component is a semiconductor device—a silicon or germanium crystal—that converts each absorbed X-ray photon into an electrical charge proportional in size to the photon's energy. The charge is then itself converted to a voltage pulse the amplitude of which is measured and recorded, and the number of "counts" for each amplitude band is accumulated in a multi-channel analyser, and subsequently employed to construct the desired diffraction pattern. Such energy-dispersive detectors are in themselves well-known, and need no further comment here, save, perhaps, to observe that a representative device is that available under the designation ORTEC from EG&G Instruments, of Wokingham, UK.

The comparison of the found measurements against the reference data—which can be derived either from actual measurements carried out on known reference materials or from computed values for those materials—can also be effected in the conventional manner, and it does not need discussing in detail here except perhaps to say, by way of example, that a useful qualitative interpretation can be effected by peak matching (of the peaks of the sample graphical representation against those of the references; this can be done by eye by an expert) while a quantitative assessment can be effected by any one of a number of computerised deconvolution methods.

As so far described the method of the invention has by implication been about the detection and measurement of diffracted X-rays that have been transmitted through the sample, this transmission being referred to as "forward scattering". It is possible, however, to have diffracted X-rays that are "back-scattered" from the sample, so that rather than be transmitted therethrough they have been reflected from the sample. Back-scattering, too, requires high intensity and high penetration capability—the X-rays are not only reflected back from the material at or adjacent the near, or illuminated, face material of the sample, they need also to be reflected back from the interior and from the far face material. The invention extends, of course, to the method when used either in a transmission system or in a reflection one. A reflection system could be of particular use in a method which analyses samples in situ—for example, the formations through which a drill is passing as it bores out the test hole for an oil or gas (or even water) well, where it would be difficult, and probably impossible, to utilise a transmission system.

The method of the invention provides a relatively fast way to analyse crystalline materials such as earth formations (as drill cores). Indeed, because it is so fast it is possible, in real time, to produce a non-destructive analysis of an entire length of a sample like a core, simply by illuminating the core in narrow slices spaced successively along its length.

First, by directing the detector collimator to point at a small spot at a known depth within the sample, and by rotating the sample, measurement by measurement, on a convenient axis (such as that normal to the plane of the input X-ray beam and the diffracted output collimated beam; in a drill core this will usually be the core axis), there may be obtained a sequence of diffraction patterns defining a narrow ring of sample material. Next, by re-directing the detector collimator to point at a spot immediately adjacent the first (in a depth sense) and repeating the rotation, there can be obtained a second sequence defining a second ring next to (and co-planar with) and contiguous with the first. And by repeating this a sufficient number of times there may be gained information about a disc of material—a "slice" through the sample. Finally, by repeating this whole process several times, each after changing the relative positions of the sample and X-ray illuminator/detector by a small amount, there may be obtained information about a series of slices along the length of the sample.

Alternatively, the beam/detector and sample relationship could be changed (preferably by moving the sample) in small steps in three mutually orthogonal—X, Y and Z—directions, so also providing a fully three-dimensional map of its composition.

Thus, for instance, if a 2.5 cm core were analysed (using the rotational slice method) in 1 mm wide slices along its length, and each single slice analysis could be effected within, say, 30 seconds, a 10 cm-long core length could be analysed in a mere 50 minutes. This compares very favourably with present-day techniques, which could well take weeks to provide the same data, and totally destroy the sample's structure in the process!

The invention naturally extends to apparatus for carrying out the method of the invention, this apparatus comprising:
- a collimated beam source of polychromatic X-ray photons of a brightness of at least $10^{15}$ photons/sec/mrad$^2$/0.1% bandwidth and energies of at least 20 keV;
- mounting means for mounting a test sample in the line of the X-rays from the source, whereby the X-rays may be diffracted by the test sample;
- collimation means for collimating some of the diffracted X-rays into a narrow parallel beam;
- an energy-dispersive detector receiving the collimated diffracted X-rays, and making measurements thereof; and
- comparison means for comparing the thus-made measurements with similar data defining known, reference materials, and thereby for determining the required characteristics of the test material.

The preferred details of the apparatus are as have already been described in connection with the method itself, and need no further comment here.

The following Examples are now given, though by way of illustration only, to show details of certain aspects of the invention. In the accompanying Drawings.

The Examples are of experiments carried out using the Daresbury UK Synchrotron Radiation Source and the Grenoble European Synchrotron Radiation Facility. In each case the experiments were of the same concept. The Grenoble facility provides X-rays that are about 50 times the brightness of the Daresbury ones.

Figure 7:
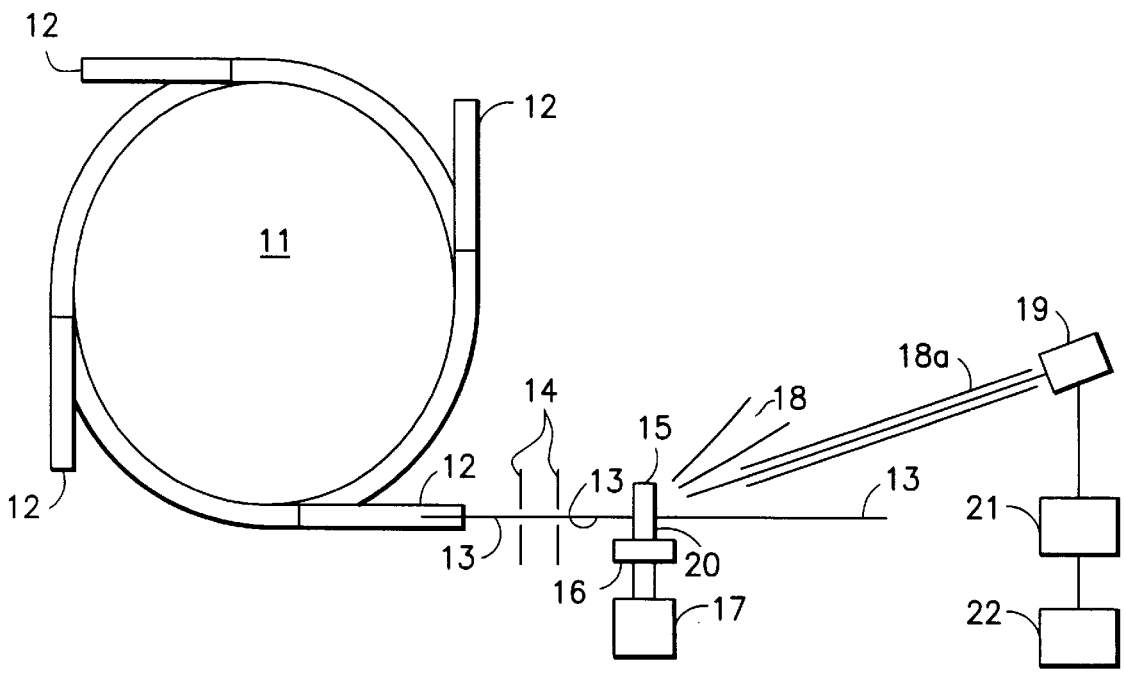
FIG. 7 shows diagrammatically the apparatus used in the method of the invention.

The apparatus used in the method of the invention is shown, diagrammatically, in FIG. 7. It consists of a synchrotron (generally 11) with a number of stations (as 12) around it, from one of which is extracted a beam (13) of polychromatic X-rays. This is passed through a sequence of slits (14) to narrow it down, and thus narrowed it is used to illuminate the sample (15). The sample is mounted on a platform (16) that can be rotated (by motor 17).

As the X-rays in the beam 13 pass into the sample material from one side they are diffracted thereby, and create a fan of forward scattered X-rays (as 18) that leave the sample from the opposing side. Positioned to look at some of these diffracted X-rays is an energy-dispersive detector (19); it is associated with a collimating tube that only lets it "see" those X-rays (18a) that have come from a point (20) within the sample. The X-ray photons the detector receives produce an electric charge that is then converted into a voltage pulse the amplitude of which is measured and recorded, and the number of "counts" for each amplitude band is accumulated in a multi-channel analyser (21), and subsequently employed to construct the desired diffraction pattern. The formed pattern—or, instead, the figures defining it—can then be compared (using a suitably-programmed computer 22) to provide the desired indication of the sample's characteristics.

In each of the following Examples the X-rays were transmitted through the sample. The X-ray beam contained photons having a wide range of energies (typically from 20 to 100 keV). Photons which satisfy the Bragg condition are scattered forward into the collimator of the fixed-angle detector. The angle is selected to provide an appropriate range of d-spacings: for example, set at 3° the d-spacing range from about 20Å to about 4Å is accessible (higher angles provide shorter d-spacings). The Daresbury equipment can incorporate three detectors aligned at different angles to provide an exceptionally large d-spacing range. Each detector (typically a high-purity Ge semiconductor device) sorts incoming photons by energy. The energy distribution of the forward-scattered radiation can be expressed in terms of the spacing between diffracting planes in the scattering mineral (the "d-spacing"). and the plot so obtained is the "powder diffraction pattern" of the sample. Peaks and line shapes provide detailed information about the crystallographic structure of the material. The diffraction pattern of a pure crystalline material is unique to that material, and positions of individual peaks and/or the entire powder pattern treated as a single entity can be used to identify unknowns. In the general case, the object whose pattern is measured is composed of a multiphasic mixture, and the pattern is interpreted qualitatively by peak matching or quantitatively by one of a variety of deconvolution methods to give an estimate of the volume fraction of the separate constituent phases.

EXAMPLE 1

Figure 1:
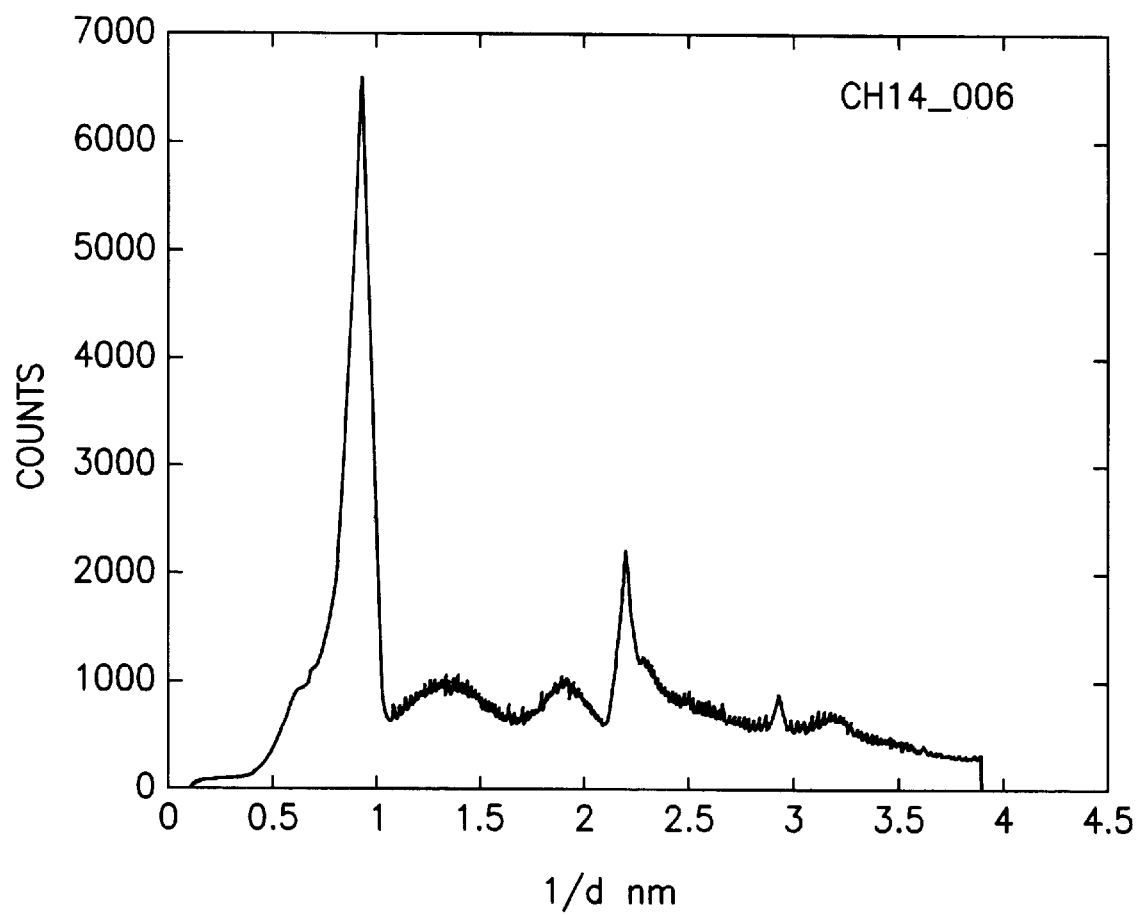
FIGS. 1–6 show graphical displays of some of the obtained results.

A Smectitic Clay (FIG. 1: Grenoble)

Approximately 1 g of dry clay (SWy-1 Wyoming bentonite, Clay Minerals Society standard) with no sample treatment was placed in a cylindrical polymer container (PEEK—polyether ether ketone—is suitable) of 10 mm diameter and 25 mm length. The X-ray powder pattern was recorded as the sample container was rotated at 20 rpm.

The recorded pattern is shown in FIG. 1. The individual lines can be interpreted in terms of known minerals.

EXAMPLE 2

Figure 2:
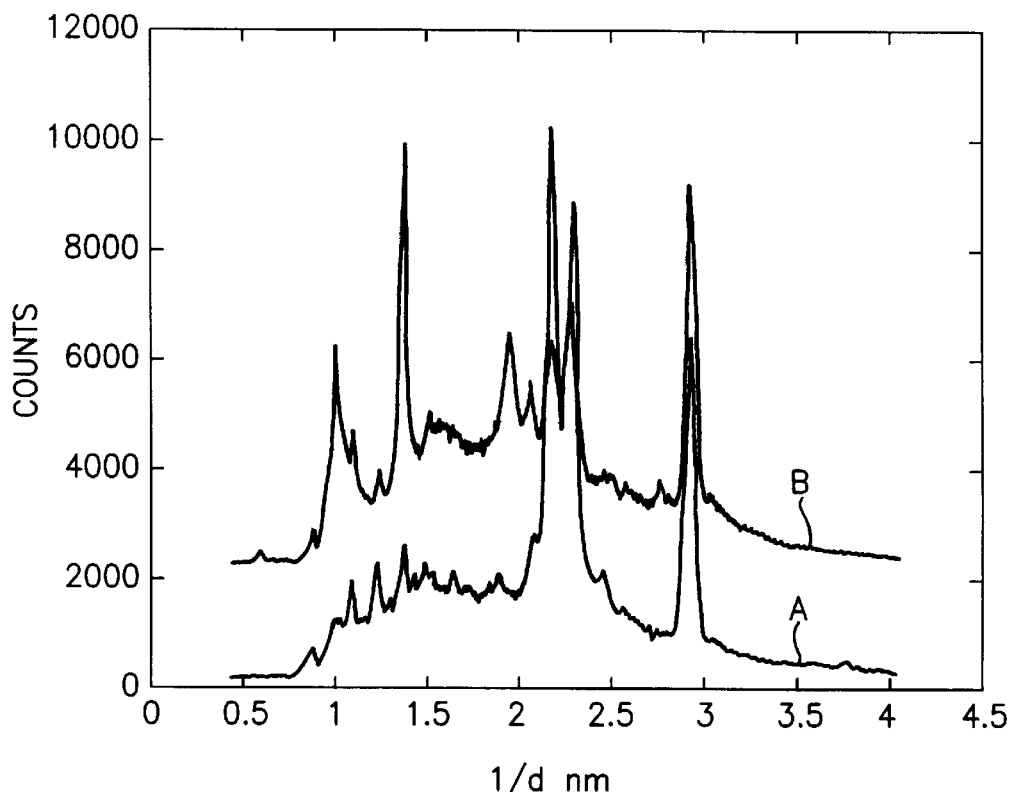

A Shale Rock (FIG. 2: Daresbury)

A sample of Pierre shale rock oriented with the bedding plane horizontal was mounted directly on a spindle rotating about a vertical axis, and the powder pattern A shown in FIG. 2 was obtained. The sample was then rotated through 90° to orientate the bedding plane vertically, and the pattern then obtained is line B of FIG. 2. The differences can be attributed to the effects of clay orientation to the bedding plane.

EXAMPLE 3

Figure 3:
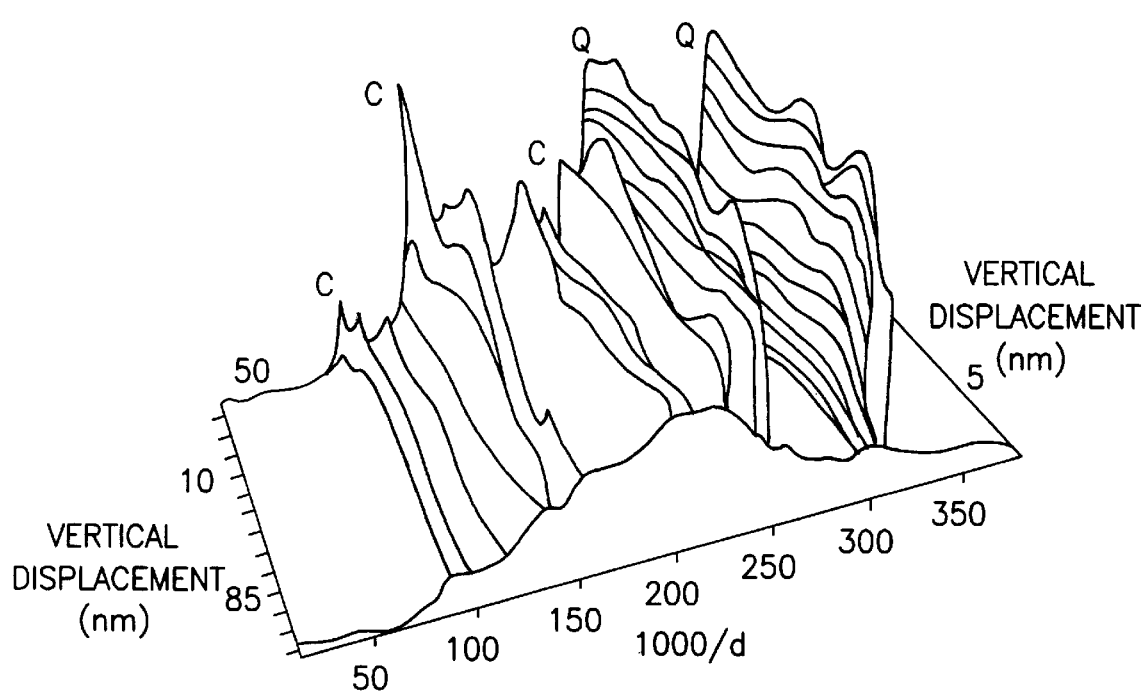

A Shale Rock (FIG. 3: Daresbury)

The same sample of shale rock as used in Example 2 was mounted in such a way that it could be translated at rightangles to the X-ray beam by a simple screw device in increments of approximately 200 micron. The powder pattern was recorded at 1 mm intervals along a total traverse of 15 mm. This is shown in FIG. 3 (in which Q represents Quartz, and C: represents Clay minerals).

Variation along the length is apparent, although the sample is relatively homogeneous.

EXAMPLE 4

Figure 4:
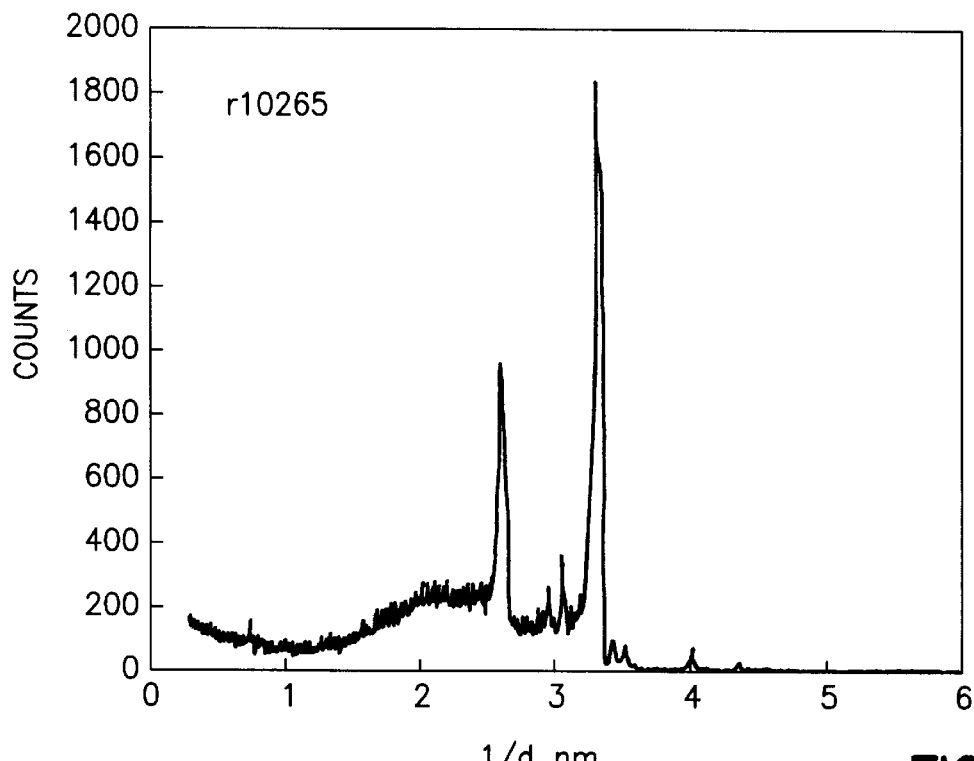

A Carbonate Rock (FIG. 4: Daresbury)

A prismatic sample of Lépine limestone of 52×50 mm cross-section was examined by the method of the invention. The photon count-rate, 3.5 kcps, was adequate to record a powder diffraction pattern (shown in FIG. 4)—essentially that of calcite—in 300 secs.

EXAMPLE 5

Figure 5:
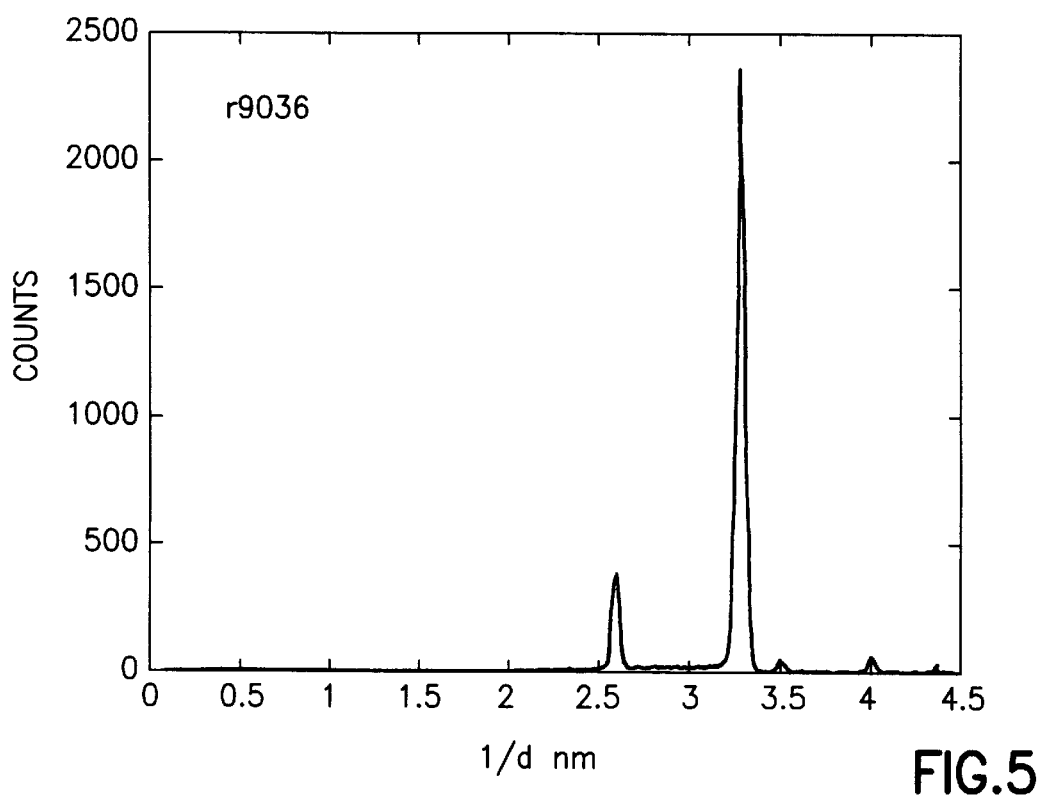

A Carbonate Rock (FIG. 5: Daresbury)

A prismatic sample of Portland limestone of dimensions 35×33 mm was examined using the method of the invention. The X-ray beam was oriented along the diagonal of the cross-section, and the results are shown in FIG. 5.

EXAMPLE 6

Figure 6:
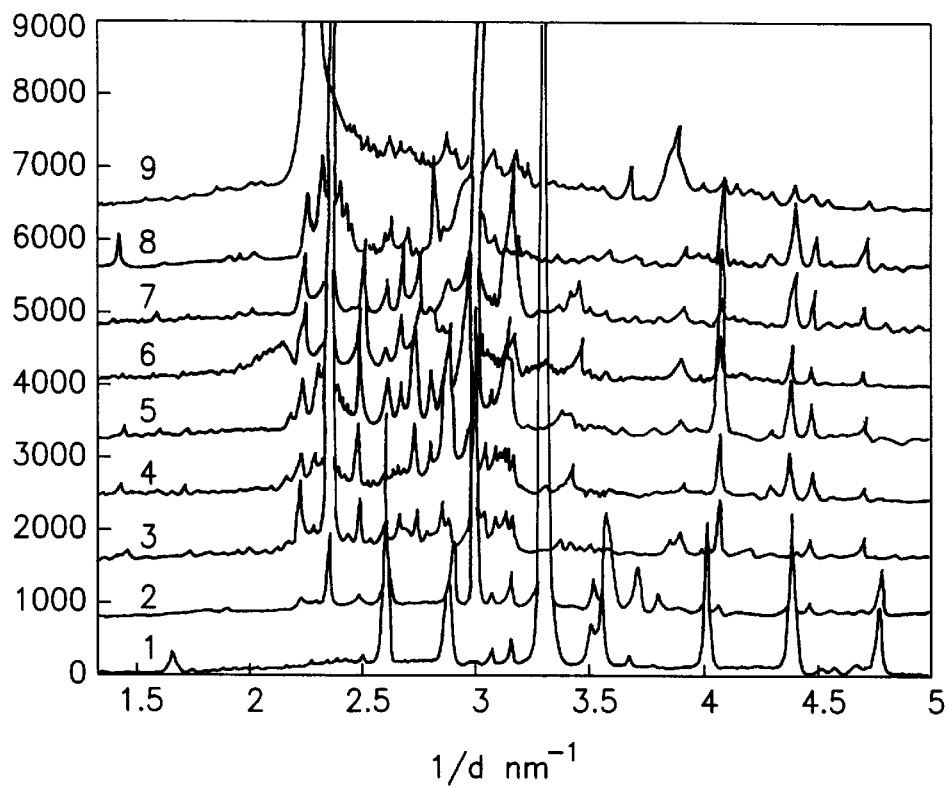

Sandstone Rocks (FIG. 6: Grenoble)

A number of different sandstones were examined using the method of the invention. Each rock was examined in the form of a cylindrical plug, 25 mm in diameter. The X-ray beam was directed at right-angles to the axis of the plug.

Each diffraction pattern was collected in 120 seconds.

The results are shown in FIG. 6, in which nine different tests have been shown on the same graph (for clarity each after the first has been positioned spaced "artificially" along the "Y" (or Counts) axis). The materials thus analysed were as follows:
1 Ketton limestone, UK
2 Tottenhoe chalk, UK
3 Fine grain sandstone from Ohio, USA
4 Carboniferous gritstone from Stancliffe, Darley Dale, UK
5 York sandstone from UK coal measures
6–7 Low permeability sandstones, borehole cores, 1781 m and 2394 m depth
8 Laminated mudrock, borehole core 4749 m depth
9 Oxford clayrock, UK

EXAMPLE 6

Five Sandstone Rocks (Grenoble)

Five sandstone rocks were examined using the technique described in Example 6. The results are shown in the Table below.

| Specimen Mineral | A | B | C | D | E |
| --- | --- | --- | --- | --- | --- |
| Quartz | 81.2 | 68.4 | 75.8 | 94.1 | 89.6 |
| Sodium feldspar | 2.3 | 13.4 | 0.4 | 0 | 0 |
| Potassium feldspar | 10.3 | 3.7 | 5.4 | 0.5 | 0 |
| Biotite | 0 | 0 | 0 | 0.2 | 0 |
| Muscovite | 15 | 1.0 | 2.0 | 0.7 | 2.9 |
| Dolomite | 0 | 0 | 0 | 0 | 0 |
| Calcite | 0 | 5.1 | 0 | 0 | 0 |
| Hematite | 0 | 0 | 0 | 0 | 0 |
| Anhydrite | 0 | 0.1 | 0.4 | 0 | 0 |
| Pyrite | 0 | 0.1 | 0.1 | 0.1 | 0 |
| Kaolinite | 3.5 | 3.6 | 8.3 | 3.9 | 7.1 |
| Smectite | 0.1 | 0 | 0 | 0 | 0 |
| Illite | 1.0 | 1.2 | 1.8 | 0.3 | 0.4 |
| Vermiculite | 0 | 3.4 | 0 | 0.5 | 0 |

In this Table the compositions are expressed as mass fractions of 15 mineral standards.
A is carboniferous sandstone, from Derbyshire, England.
B is carboniferous sandstone, from W Yorkshire, England.
C is laminated silty mudstone
D,E are medium-grained sandstones (oilfield plugs).

The obtained diffraction patterns were compared with similar patterns obtained under the same conditions from a set of 15 pure minerals (quartz, sodium feldspar, etc). Using a least-squares regression procedure there was found, for each rock sample test pattern, the best matching "comparison" pattern formed by adding the patterns of the mineral standards in appropriate proportions. The sample can then be identified as being made up of those minerals in those proportions.

I claim:

1. A method of determining characteristics of a test crystalline material in which method a sample of the material is illuminated with a collimated beam of polychromatic X-ray photons, to produce diffracted X-rays, measurements are taken of the produced diffracted X-rays with an energy-dispersive detector receiving them via a collimator, and by comparing the found measurements with similar data defining known, reference materials, there are determined the required characteristics of the test material, which method is characterized in that the test crystalline material is a drill core rock sample of a cylindrical shape having a core axis;

the beam of X-ray photons has a brightness of at least $10^{15}$ photons/sec/mrad$^2$/0.1% bandwidth and energies of at least 20 keV;

and further characterized in that the relative position of the sample and the beam is moved in the direction of the core axis so as to determine characteristics of a plurality of portions along the core axis of the rock sample.

2. A method as claimed in claim 1, wherein the test material is a length of the drill core.

3. A method as claimed in claim 1, wherein for a high resolution system the X-ray beam is from 0.5 to 0.02 mm wide.

4. A method as claimed in claim 1, wherein the intensity of the X-rays is at least $10^{17}$ photons/sec/mrad$^2$/0.1% bandwidth.

5. A method as claimed in claim 1, wherein the source of the X-rays is a synchrotron.

6. A method as claimed in claim 1, wherein the energy-dispersive detector is a semiconductor device.

7. A method as claimed in claim 1, wherein there are detected and measured those diffracted X-rays that have been transmitted through the sample.

8. A method as claimed claim 1, wherein:

first, by directing the detector collimator to point at a small spot at a known depth within the sample, and by rotating the sample, measurement by measurement, on a convenient axis, there is obtained a sequence of diffraction patterns defining a narrow ring of sample material;

next, by re-directing the detector collimator to point at a spot immediately adjacent the first (in a depth sense) and repeating the rotation, there is obtained a second sequence defining a second ring next to (and co-planar with) and contiguous with the first;

and by repeating this a sufficient number of times there is gained information about a disc of material—a "slice" through the sample;

and finally, by repeating this whole process several times, each after changing the relative positions of the sample and X-ray illuminator/detector by a small amount, there is obtained information about a series of slices along the length of the sample.

9. Apparatus for use in a method of determining characteristics of a drill core rock sample comprising:

a collimated beam source of polychromatic X-ray photons of a brightness of at least $10^{15}$ photons/sec/mrad$^2$/0.1% bandwidth and energies of at least 20 keV;

mounting means for mounting a cylindrically shaped solid drill rock sample core having a core axis in the line of the X-rays from the source, whereby the X-rays may be diffracted by the test sample;

collimation means for collimating some of the diffracted X-rays into a narrow parallel beam;

an energy-dispersive detector receiving the collimated diffracted X-rays, and making measurements thereof;

comparison means for comparing the thus-made measurements with similar data defining known, reference materials, and thereby for determining the required characteristics of the test material; and means for changing the relative positions of the rock sample and the beam so as to cause the rock sample to translocate in the direction of the core axis.

10. Apparatus as claimed in claim 9, wherein the X-ray source provides a beam of from 0.5 to 0.02 mm wide.

11. Apparatus as claimed in claim 9, wherein the X-ray source provides X-rays of at least $10^{17}$ photons/sec/mrad$^2$/0.1% bandwidth.

12. Apparatus as claimed in claim 9, wherein the X-ray source is a synchrotron.

13. Apparatus as claimed in claim 9, wherein the energy-dispersive detector is a semiconductor device.

14. Apparatus as claimed in claim 9, wherein the mounting means is a table on which the test sample can be secured, which table is moveable so as to cause the sample to rotate about an axis and so as to cause the sample to translocate along a line.

15. Apparatus as claimed in claim 14, wherein the rotation and translocation are stepwise.

* * * * *